United States Patent [19]

Korhonen et al.

[11] Patent Number: 5,125,016
[45] Date of Patent: Jun. 23, 1992

[54] PROCEDURE AND MEASURING APPARATUS BASED ON X-RAY DIFFRACTION FOR MEASURING STRESSES

[75] Inventors: Matti Korhonen; Veikko Lindroos, both of Espoo, Finland

[73] Assignee: Outokumpu Oy, Finland

[21] Appl. No.: 530,896

[22] Filed: May 30, 1990

Related U.S. Application Data

[63] Continuation-in-part of Ser. No. 740,073, May 20, 1985, abandoned.

[30] Foreign Application Priority Data

Sep. 22, 1983 [FI] Finland .................... 833393

[51] Int. Cl.$^5$ .......................................... G01N 23/20
[52] U.S. Cl. ........................ 378/72; 378/70; 378/197; 378/79; 250/370.10
[58] Field of Search ............ 378/72, 124, 197, 79, 378/70; 250/370, 370.10

[56] References Cited

U.S. PATENT DOCUMENTS

| | | | |
|---|---|---|---|
| 2,462,374 | 2/1949 | Firth ........................ | 378/72 |
| 3,529,161 | 9/1970 | Oosthoek et al. ............ | 250/370.10 |
| 3,617,705 | 11/1971 | Takano ...................... | 378/72 |
| 3,843,886 | 10/1974 | Stumpel et al. ............. | 250/370.10 |
| 3,863,072 | 1/1975 | Garin et al. ................ | 250/370.10 |
| 4,095,103 | 6/1978 | Cohen et al. ............... | 378/72 |
| 4,128,762 | 12/1978 | Nagao et al. ............... | 378/72 |
| 4,147,933 | 4/1979 | Rougeot et al. ............ | 250/370.10 |
| 4,245,158 | 1/1981 | Burstein et al. ............ | 250/370 |
| 4,769,546 | 9/1988 | Kniffler et al. ............. | 250/370.10 |
| 4,804,848 | 2/1989 | Horiba et al. .............. | 250/370.10 |
| 4,959,548 | 9/1990 | Kupperman et al. ........ | 378/72 |

FOREIGN PATENT DOCUMENTS

61248 12/1981 Finland .

OTHER PUBLICATIONS

J. E. Lamport et al., A Large Area Circular Position Sensitive Si Detector, Nuclear Instruments and Methods 134 No. 1 (1976) 71-76.

Alvin Kanofsky, Solid State Micro-Detectors for High Energy Experiments, Nuclear Instruments and Methods 140 No. 3 (1977) 429-432.

Primary Examiner—Janice A. Howell
Assistant Examiner—Kim-Kwok Chu
Attorney, Agent, or Firm—Steinberg & Raskin

[57] ABSTRACT

Procedure based on X-ray diffraction for measuring the stress state of metals, in particular austenitic steels. In the procedure the detector surface (10) is inclined about an axis (A—A) lying on the surface of the sample (20) being examined which is substantially perpendicular to the direction of the stresses ($\sigma_{xx}$) being examined. By means of the detector surface (10) the diameters ($2S_{ax}$) of the so-called Debye rings in the direction of the surface being examined are recorded at two or several inclination angles ($\psi$). The detector surface (10) has arcuate shape, as viewed in the direction (B—B) at right angles against the inclination axis (A—A), and in the procedure is used such as arcuate detector surface (10) elongated in the direction of said inclination axis (A—A) and narrow enough in the opposite direction that an inclination angle ($\psi$) of the detector surface (10) large enough in view of the procedure's implementation is feasible. In the procedure a detector surface (10) is used by which the x-rays reflected from the sample are converted to photosignals, and that on the basis of these photosignals the stresses to be measured are determined. Also disclosed is a measuring instrument in which the detector surface (10) is located symmetrically on both sides of the collimator, and the detector surface (10) is provided with elements (10a, 10b, 41) by which the X-ray radiation incident on the detector surface is converted into photosignals, and the apparatus further comprises a unit or units with which the stresses to be measured are derived on the basis of the photosignal.

10 Claims, 5 Drawing Sheets

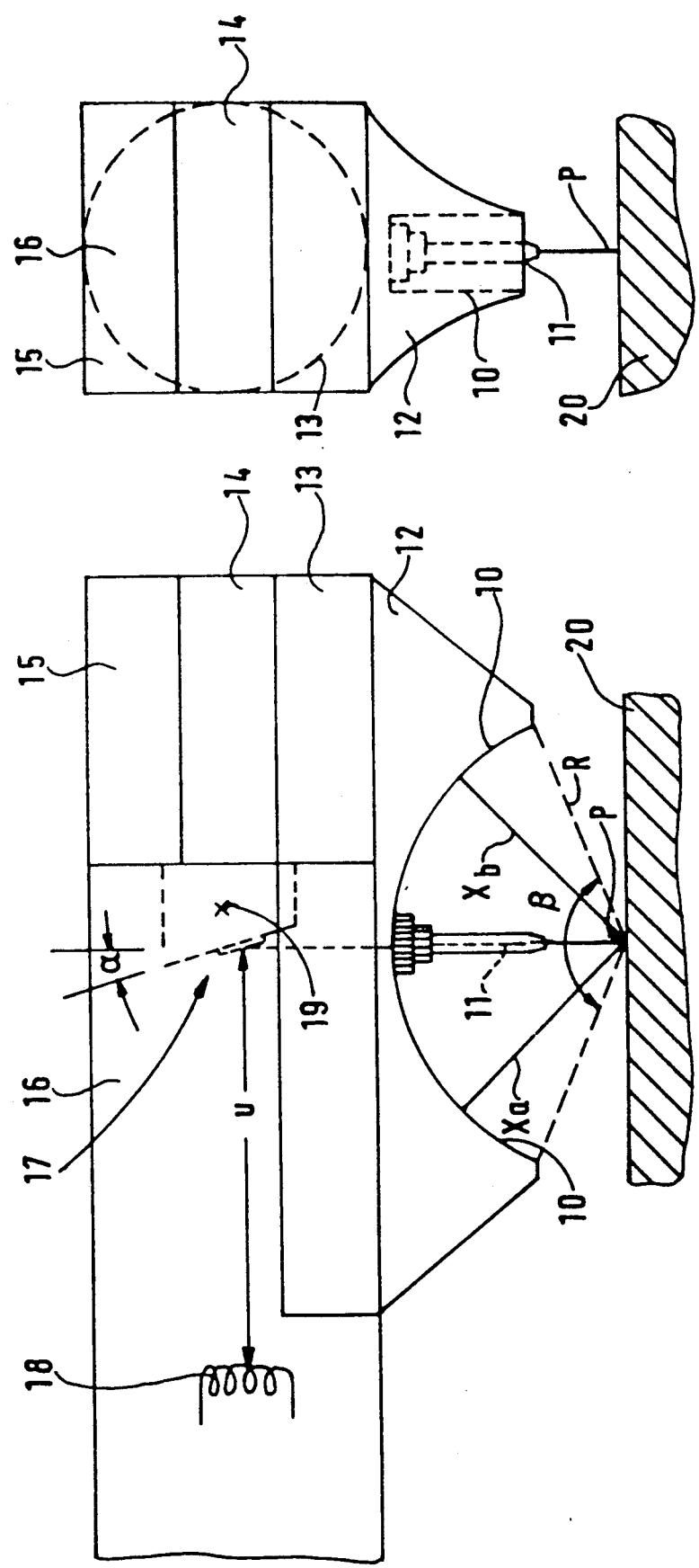

PROCEDURE AND MEASURING APPARATUS BASED ON X-RAY DIFFRACTION FOR MEASURING STRESSES

CROSS REFERENCE TO RELATED APPLICATION

This application is a continuation-in-part of pending application Ser. No. 06/740,073, filed May 20, 1985, now abandoned, entitled "PROCEDURES AND MEASURING INSTRUMENT BASED ON X-RAY DIFFRACTION FOR MEASURING STRESSES".

BACKGROUND OF THE INVENTION

The present invention concerns a procedure and apparatus based on X-ray diffraction for measuring stress states in metals. More particularly, the invention relates to a procedure for measuring stress states in austenitic steels or the equivalent. In the apparatus of the invention, a detector means is inclined about an axis lying on the surface of the specimen under examination which is substantially perpendicular to the orientation of the stresses to be studied. By mediation of the detector means, the diameters parallel to the surface under examination of the so-called Debye rings, or the equivalent, are recorded at two or more angles of inclination. The detector, as viewed in the direction at right angles against the inclination axis, has an arcuate shape. The detector means is elongated in the direction of the inclination axis and narrow enough in the opposite direction to make feasible an inclination angle of the detector means great enough to carry out the invention.

The invention further concerns a measuring instrument for carrying out the procedure, comprising an X-ray tube disposed together with its ancillary apparatus to be rotated about the inclination axis, said axis passing through the point to be examined of the specimen to be examined. As viewed in a direction at right angles with the inclination axis, the detector means is an arcuate shape, preferably that of a circular arc.

The need for non-destructive stress measurement has increased considerably in recent years. A non-destructive stress measuring method in more extensive use is based on the diffraction of X-rays in crystalline matter. The greatest shortcoming of the measuring equipment is its complex design and great bulk, impeding its application in field conditions.

Stress measuring methods based on X-ray diffraction measure the stresses in the surface of crystalline material. The depth of penetration of the X-rays is on the order of 5 to 24 μm. The stresses in the surface are significant with a view to the durability of structures, because damage usually starts in the superficial layers, as exemplified by stress corrosion, brittle fracture, fatigue, etc.

According to international estimates, the annual losses from material-technological faults amount to about 50 billion Finnish marks, a great part thereof caused by residual stresses.

Residual stresses always arise as a result of inhomogeneous deformation, which may be a consequence of the following factors, among others: working, temperature differences, phase transformation, different thermal expansion coefficients of different phases. Residual stresses are incurred in metal treatments such as, for example, welding, heat treatments and machining, for example, by grinding.

Residual stresses are usually divided into two groups depending on their distance of influence. These groups are macrostresses and microstresses. The sphere of influence of macrostresses extends, at a minimum, over several grains, whereas microstresses are concentrated in the region of one grain. Macrostresses are measured by X-ray diffraction, and are either compressive or tensile residual stresses. Tensile stresses are unfavorable in the surface from the viewpoint of structures. On the other hand, compressive stresses improve, for example, the fatigue strength of metals, and it is therefore often desirable to achieve a compressive stress in the surface of metallic components. The most important methods by which a state of compressive stress can be produced are ball blasting, rolling, hammering, and in general any method by which a metal surface is plastically deformed.

There has been comparatively little practical application of non-destructive stress measuring methods and means of the prior art.

Finnish Pat. No. 61248 discloses an improved camera procedure utilizing non-bulk apparatus of simple design, compared with diffractometer apparatus that was in general use theretofore, to eliminate the aforementioned disadvantages.

There are in principle two types of stress measuring instruments based on X-ray diffraction. These types are camera and diffractometer apparatus. The simplest and smallest instrument construction is achieved in the camera construction, but its drawback is the comparatively long time required to expose and develop the film. With diffractometers, the X-ray intensity is measured as a function of the 2θ angle with a proportional or scintillation counter. A scan must be run with the counter over a given 2θ angle range, and this requires an accurate goniometer apparatus. For this reason, diffractometers are relatively bulky, complex and expensive instruments as far as field work is concerned. It has been possible somewhat to reduce the size of diffractometers and to increase their speed with the aid of so-called location-sending detectors.

Since the use of the camera method disclosed in Finnish Pat. No. 61248 is associated with a comparatively long time required for exposing and developing the film, the object of the present invention is to develop a stress measuring procedure and apparatus which has a bulk on the same order as the camera construction, but which is substantially faster in use.

In order to attain the aims stated, and others which will become apparent later on, the invention utilizes a detector means by which the X-rays reflected from the specimen are converted into photosignals, and the stresses to be measured are determined from these photosignals.

SUMMARY OF THE INVENTION

The principal object of the invention is to provide stress measuring apparatus based on X-ray diffraction, which apparatus measures stress considerably faster than does the prior art camera method.

An object of the invention is to provide stress measuring apparatus based on X-ray diffraction, which apparatus measures stress in a period of a few seconds to one minute, as opposed to the time of more than 5 minutes required by the prior art camera method, plus development time for the film.

Another object of the invention is to provide stress measuring apparatus based on X-ray diffraction, which apparatus is portable and performs measurements under actual field conditions, so that it may be used in offshore and maritime technology, energy production, heavy mechanical engineering, mining and processing.

The stress measuring apparatus and procedure of the invention based on X-ray diffraction permits the addressing of the following points.

1. The occurrence and quantity of residual stresses produced by welding and heat treatment.
2. The necessity for stress relief annealing and its efficiency in welds and castings.
3. Aiding the design of structures subjected to load.
4. Acceptance inspections and reinspections of load-bearing structures such as, for example, pressure vessels, reactors, etc.

In accordance with the invention, apparatus for measuring stresses includes detector means symmetrically disposed on both sides of the X-ray collimator and has components which convert the X-radiation striking the detector into photosignals. The apparatus also includes means for deriving the stresses to be measured from the photosignals.

The apparatus and procedure of the present invention for measuring stress has been derived from the improved camera procedure of the aforementioned Finnish Pat. No. 61248, which has the advantage of ideal Schultz-type focussing, which minimizes the focussing and absorption errors. Another factor which reduces the random errors and many apparatus errors is that in the improved camera procedure instead of the Debye rings their diameters are measured. In the present invention, the film which had to be used in Finnish Pat. No. 61248 is replaced with a scintillation coating, or an equivalent integrated coating circuit, which converts the X-rays into photosignals. Since the intensity of the diffracted X-rays is low and the efficiency of a scintillation coating is only 15 to 20%, for example, it is advantageous to amplify the light. The light is transferred from the scintillation coating to the amplifier e.g., by the aid of optical fibers.

Instead of scintillation coatings and separate electronic units, it is possible to use detector means prepared by the integrated circuit manufacturing technique. This permits the direct provision of an electrical signal which can be recorded with a fast scanner, subsequently supplying the signal thus obtained to the computer, without the need for optic fibers. Instead of a scanner, it is also possible to use a digital counter for recording the amount of voltage pulses arriving from detector means made by the integrated circuit technique. It is possible by this technique to realize a detector means extending over such a large sector that the slide means, hereinafter described, by which said detector means is displaced, is not absolutely needed.

BRIEF DESCRIPTION OF THE DRAWINGS

For a fuller understanding of the invention, reference is had to the following description, taken in connection with the accompanying drawings, in which:

FIG. 6 is a view, in elevation, of detector means of the embodiment of FIG. 5 of the invention;

FIG. 7 is an end view of the detector means of FIG. 6;

DESCRIPTION OF THE PREFERRED EMBODIMENTS

Figure 1A:
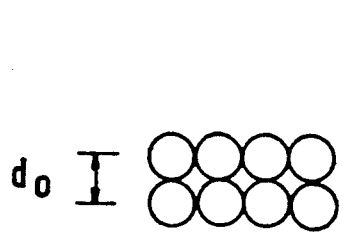
FIG. 1A is a schematic diagram of the average spacing of the atomic planes of a given substance in a stress-free state.
Figure 1B:
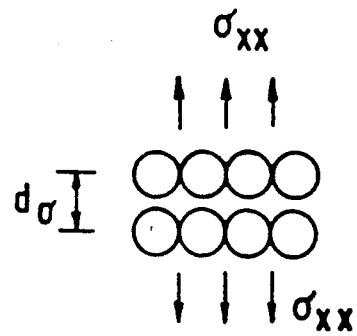
FIG. 1B is a schematic diagram of a substance in a state subject to stress $\sigma_{xx}$.
Figure 2:
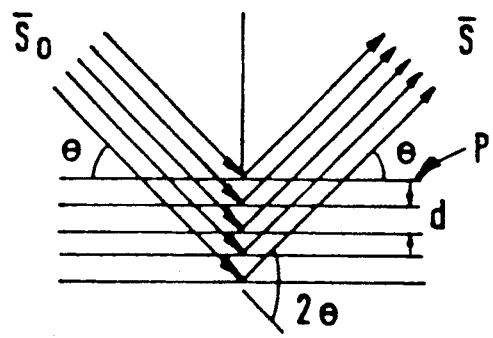
FIG. 2 illustrates the principle of reflection of X-rays from the object under examination.

In the X-ray apparatus and method constituting the basis of the invention, the spacing d of atomic planes is used as the measuring length (FIG. 1). Monochromatic X-rays having the wavelength $\lambda$ are reflected by the atomic planes when striking the planes under the angle $\theta$, which is formed by Bragg's law $$2 d \sin \theta = \lambda \tag{1}$$

as shown in FIG. 2.

In the case depicted in FIG. 1, the normal stress $\tau_{xx}$ perpendicular to the atomic planes increases the atomic plane spacing from $d_o$ to $d_\tau$. With the aid of Bragg's law, both distances, $d_o$ and $d_\tau$, can be calculated using the respective Bragg angle $\theta$, which is measured by X-ray diffraction. The normal deformation is thus calculable by the equation $$e_{xx} = \frac{d - d_o}{d_o} \tag{2}$$

The corresponding stress $\sigma_{xx}$, which causes the deformation $e_{xx}$, is then determinable with the assistance of Hooke's law $$\sigma_{xx} = E \, e_{xx}, \tag{3}$$

where E is the modulus of elasticity.

Figure 3:
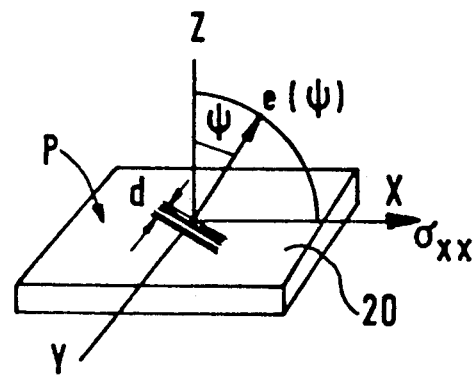
FIG. 3 is a schematic diagram illustrating the various parameters used in the X-ray apparatus.

More generally, the X-ray apparatus and method produces the normal stress component $\sigma_{xx}$ in the selected direction x when at least two deformations $e(\Psi)$ in the xz plane are measured (FIG. 3). From Hooke's general law $$\sigma_{xx} = \frac{E}{1-\nu} \frac{\epsilon(\Psi_2) - \epsilon(\Psi_1)}{\sin^2 \Psi_2 - \sin^2 \Psi_1} \quad (4)$$

where $\nu$ is the Poisson ratio.

According to the general theory of elasticity, the entire stress state is defined when three stress components with different directions are known.

When, in accordance with the starting point of the invention, the beams of the reflections are recorded on a cylindrical or equivalent detector surface 10 of the detector means paralleling the diameter A—A to be measured, the reflections from austenitic steels, such as, for example, $(220)_{Cr-K\alpha}$ and $(310)_{Cr-K\beta}$, can be recorded inclination angles $\Psi_1$ and $\Psi_2$ differing sufficiently (equation (4)) so that adequate accuracy is achieved in the stress measurement.

Since the $2\theta$ angle (FIG. 2) is slightly too small, however, the Debye diameters must be measured with corresponding greater accuracy in order to attain the accuracy which is characteristic of the common camera methods of the prior art, when determining the stress state in steels. This is, in fact, possible in the improved camera method constituting the basis of the invention, because in this method the images made under different inclinations can be focused, since the absorption factor is not dependent on the inclination, since many apparatus-specific factors introduce no error when diameters are being measured, and since the random errors of the $2\theta$ angle found via diameter measurement are less than those incurred in measuring vertical beams.

It is thus understood that by the improved camera method of the invention in which a specific detector surface appropriate for examining austenitic steels (more specifically described hereinafter) is used, it is possible to measure the stress states of austenitic steels with an accuracy which is typical when examining the stress states of ferritic steels by common, known camera methods by which determination of the stress states in austenitic steels with sufficient accuracy has been impossible heretofore.

Figure 4:
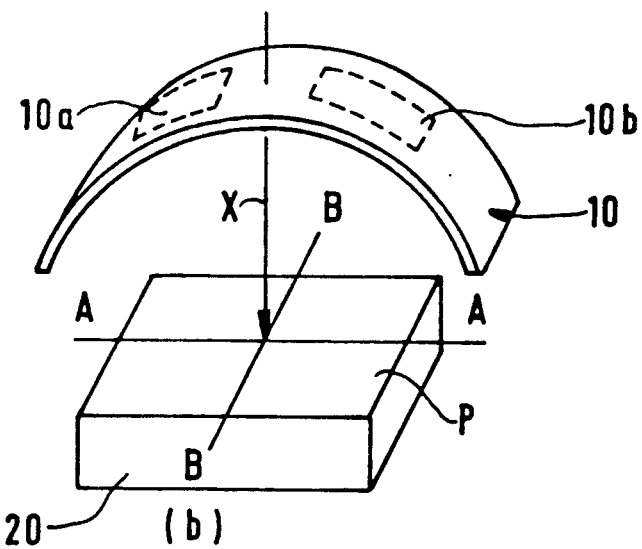
FIG. 4 is a perspective view of detector means of the invention shaped like part of a cylinder.

The embodiment of the invention presented in FIGS. 4 to 9 comprises an X-ray tube 16 mounted to be rotatable about the axis of rotation A—A indicated in FIG. 4. The axis A—A is perpendicular to the strain effect direction of the stress to be measured. The axis A—A passes through, or close to, the point P to be examined of the specimen 20 to be examined. For swivelling the apparatus about the axis A—A, the mounting of the tube includes a rotatable axle having a round cross-section around which a tightenable and lockable ring (not shown in the FIGS.) is provided, as can be seen in Finnish Pat. No. 61248.

In the apparatus of the invention, the X-ray film of Finnish Pat. No. 61248 and its cassette are replaced by a detector or detector means 10 provided with scintillation coatings 10a and 10b and having an arcuate shape. On the surface 10 of the detector, the scintillation coatings 10a and 10b are located symmetrically on either side of an X-ray collimator 11, as shown in FIG. 6.

The X-ray tube 16 comprises an incandescent cathode 18 and an anode 17 on which the electrons accelerated by voltage U impinge, generating X-radiation, as known in the art. The voltage U is usually in the range from 40 to 50 kV. The anode 17 is mounted on a supporting and cooling structure 19. The anode surface is inclined at an angle $\alpha$ with the axis of the collimator 11. The angle $\beta$ is appropriately about 6°, whereby a desirable concentration of X-rays X is provided on the specimen 20. The anode 17 of the X-ray tube 16 may comprise, for example, a Cr anode. The X-ray tube 16 includes cooling means 15 known in itself in the art. As shown in FIGS. 6 and 7, the scintillation coatings 10a and 10b of the detector means are located on the radius R under the angle $\beta$ with the point P to be examined as the center. Encapsulated fiber optics 12 are connected to the scintillation coatings 10a and 10b, and a preamplifier 13 and a semiconductor detector 14 are provided with the X-ray tube 16.

Figure 5:
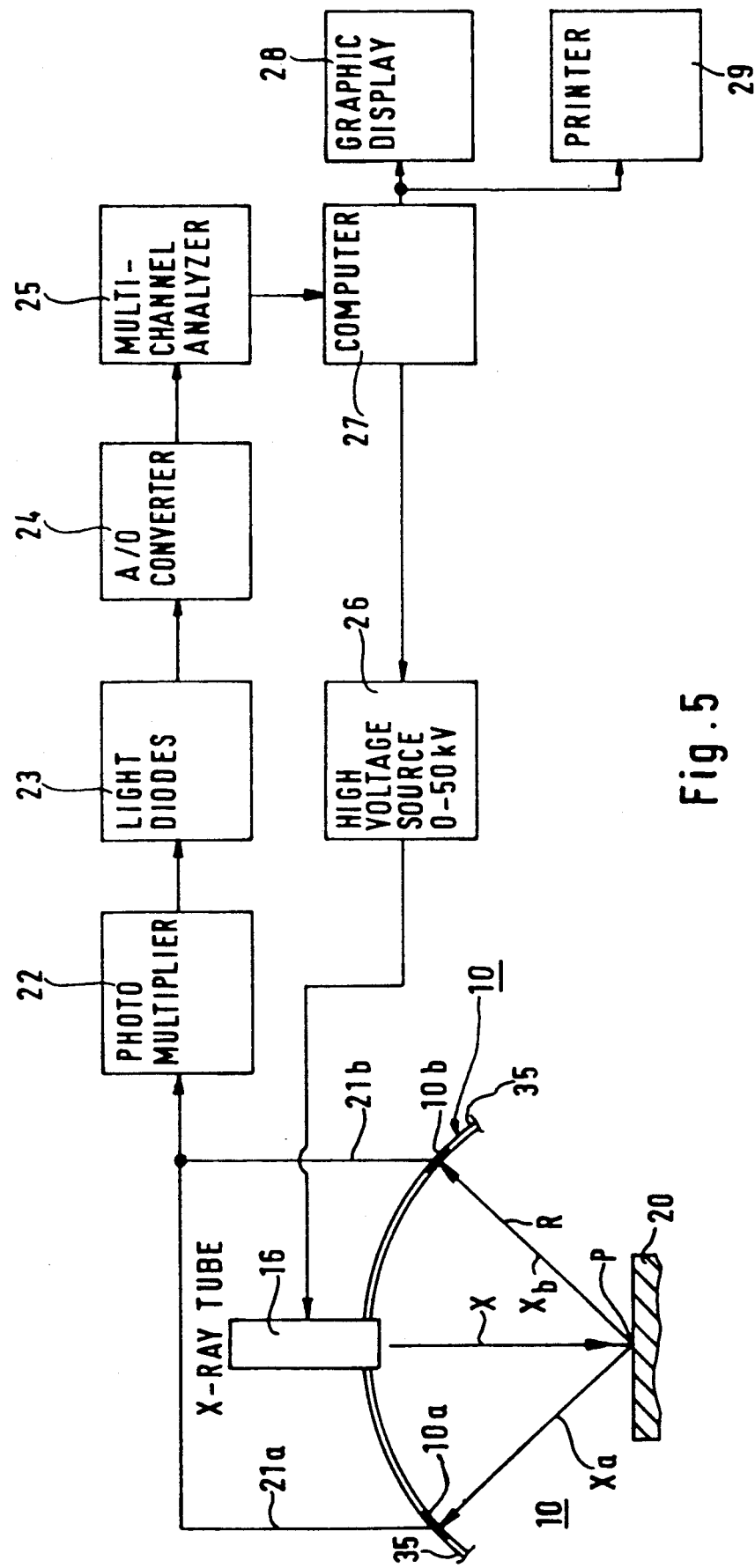
FIG. 5 is a block diagram of an embodiment of the apparatus of the invention illustrating the principle of operation of the invention.

In the embodiment of FIG. 5 of the apparatus of the invention, the scintillation coatings 10a and 10b are connected by fiber optic light cables 21a and 21b to the image intensifier 22, which operates as an amplifier in a manner known in the art. The intensity of the light signal obtained from the image intensifier 22 is measured by a series of silicon photodiodes 23. In Finnish Pat. No. 61248, the equivalent measurement, that is, the intensity distribution of the X-rays, is determined from the film via a photometer. The results of the measurement from the silicon photodiode array 23 are fed to an analog to digital converter 24 and then to a multi-channel analyzer 25. The information supplied by the multi-channel analyzer 25 is supplied to a computer 27 which is connected to a graphic results display 28 and a printer 29. Furthermore, the computer 27 controls by its program a high voltage source 26 of the X-ray tube to obtain a suitable operating sequence for the measuring apparatus.

Figure 8:
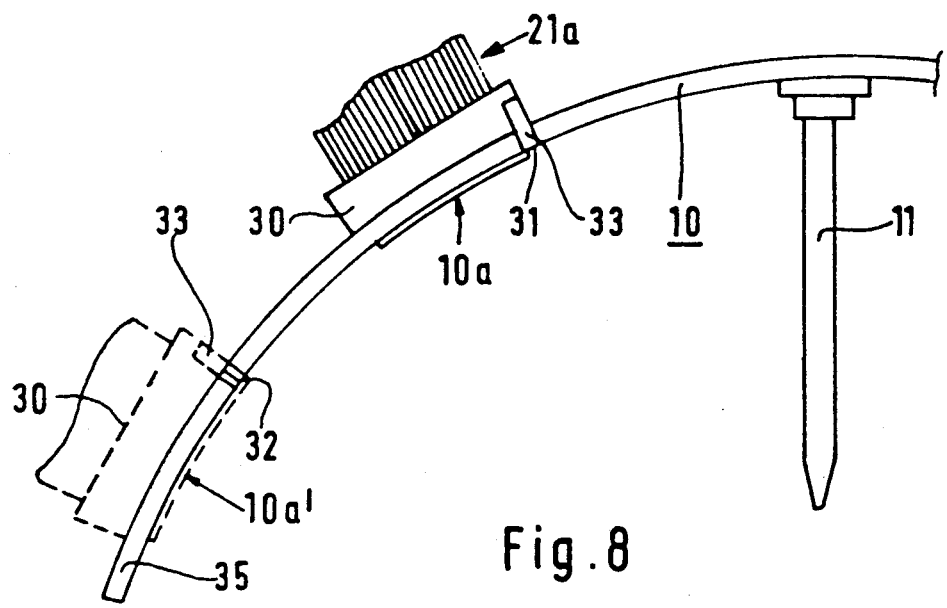
FIG. 8 is a view, on an enlarged scale and in elevation, of part of the detector means of the invention having scintillation coatings for receiving X-radiation reflected from the specimen.
Figure 9:
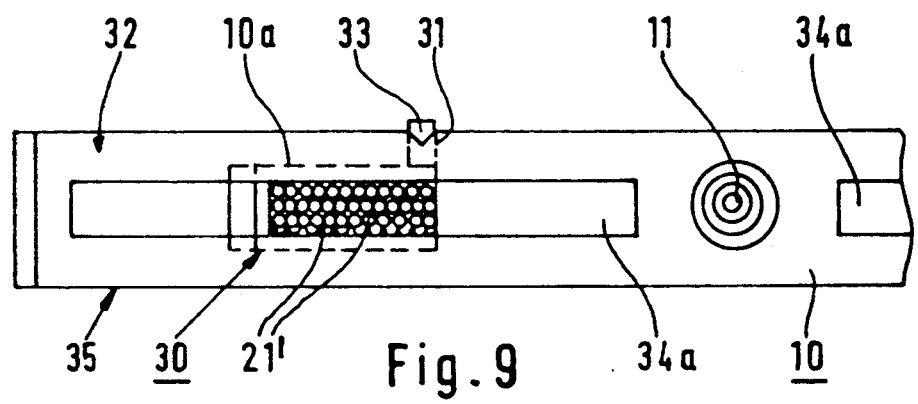
FIG. 9 is a view of the detector means of FIG. 8, seen from the side of the light-sensitive surface of the scintillation coating.

FIGS. 8 and 9 disclose the detector means 10 in greater detail. The detector 10 consists of a conductor or guide 35 bent to a radius of curvature R and having its center at the point P to be examined by the specimen 20. Symmetrical grooves 34a and 34b are provided in the conductor 35 on both sides of the X-ray collimator 11 and slide components 30 of the scintillation coatings 10a and 10b are mounted to slide in these grooves. The scintillation coatings 10a and 10b are provided directly at the ends of the optic fiber cables 21a and 21b by vaporizing, for example. In this manner, cables 21a and 21b are rectangular, for example, with a size of about $2 \times 1$ mm. In FIG. 9, the ends 21' of the cables are shown in greatly exaggerated size in order to enhance the clarity of illustration.

As shown in FIGS. 8 and 9, the slide component 30 is held by its clamp 33 in the upper position in which the pointed tongue of said clamp locks said slide component in the position determined by an upper locking groove 31 of the guide 35. It is possible in this upper position to observe X-ray reflections Xa and Xb when the angle $2\theta$ is about 156° to 160°. This position is appropriate, for example, for $\alpha$ —Fe, Ti, Al measurements. The slide components 30 of the scintillation coatings 10a and 10b may also be moved into the lower position, shown by broken lines in FIG. 8, where the clamps 10b can also be moved into the lower position 30', where the clamps 33 lock the slides 30' and their scintillation coatings 10a', and 10b', in conjunction with the grooves 32 in the guide 35. In this lower position, where the angle $2\sigma$ is about 126° to 130°, it is possible to perform measurements on $\theta$ —Fe,Ni alloys.

The improved camera method of the invention is now described:

The diameters 2S of the Debye rings in the direction of the axis are measured directly via the scintillation coatings 10a and 10b. The tangent of the reflection angle $180° - 2\theta = 2\theta$ is obtained from the diameters via the equation.

$$\tg 2\theta = \frac{2S}{2D} \tag{5}$$

where D is the distance between the test specimen 20 and the surface of the detector 10. The deformations are then obtained by the equation $$\varepsilon(\Psi) = \frac{\cos^2 2\theta}{2\tg\theta}(\tg 2\theta_\Psi - \tg 2\theta_0) \tag{6}$$

and when this is substituted in equation (4), the operating equation of the procedure and apparatus of the invention:

$$\sigma_{xx} = K_2(S_{\Psi 2} - S_{\Psi 1}).$$

wherein the stress coefficient is $$K_2 = \frac{E \cos^2 2\theta}{2D(1 - v)\tg} \cdot \frac{1}{\sin^2 \Psi_2 - \sin^2 \Psi_1} \tag{8}$$

Figure 10:
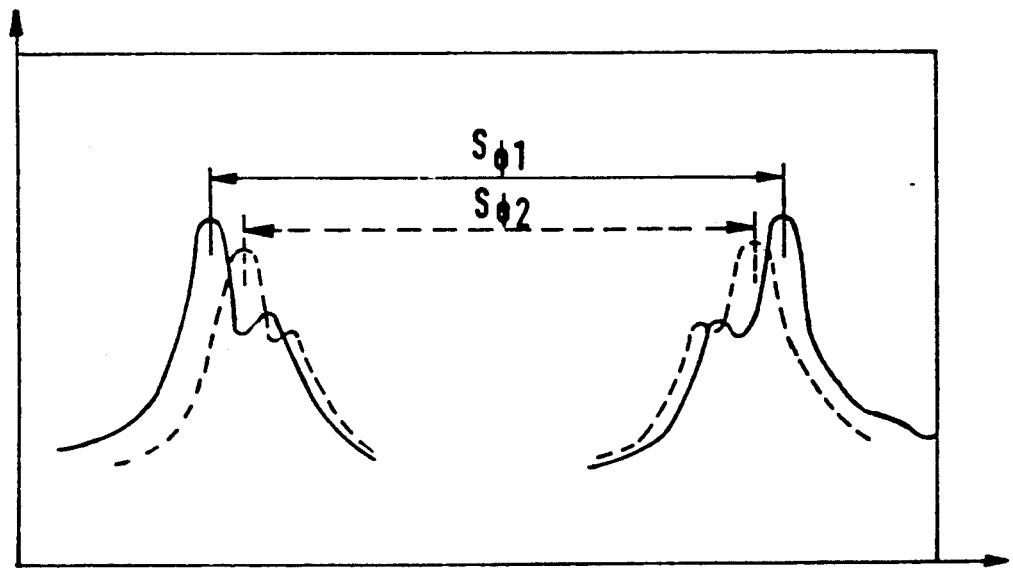
FIG. 10 is a graphical presentation illustrating an example of the graphic display obtained in a measurement at the display terminal connected to the computer.

FIG. 10 shows the graphic representation obtained on the display screen in the measurements, one graph at a time being displayed. In FIG. 10, the ordinate axis is the number of pulses per channel received from the multi-channel analyzer 25 and the abcissa axis represents the number of channels. When the distance S between peaks of the graphs in FIG. 10 is measured for two different inclination angles $\Psi$, the stress can be calculated from the equation (7) above. The computer 27 may be programmed to calculate directly the measured stresses on the basis of the foregoing equations, and the results of stress measurement are obtainable directly from the graphic display 28 and/or the printer 29.

Figure 11:
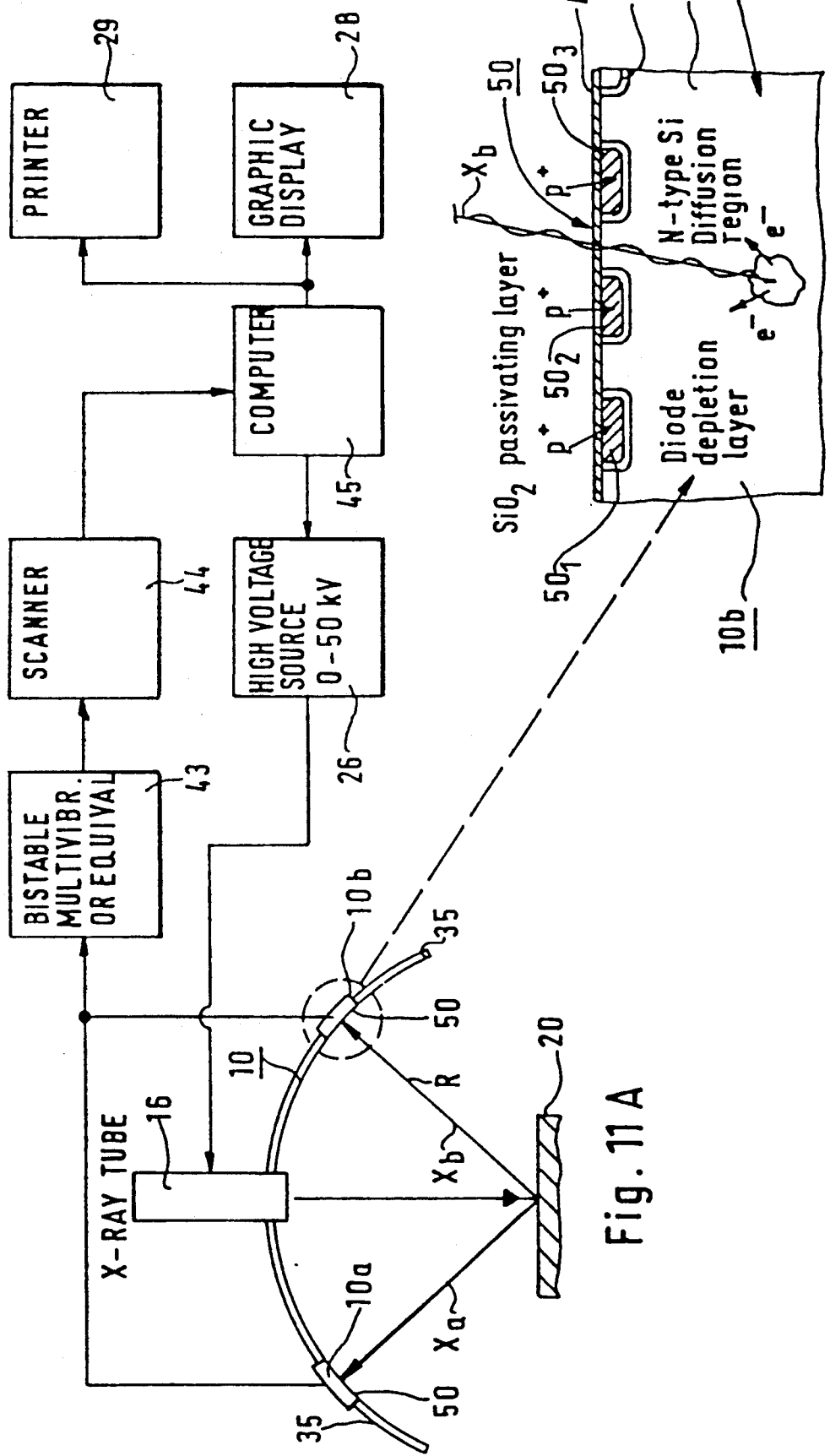
FIG. 11A is a block diagram of another embodiment of the apparatus of the invention wherein the detector means includes solid state technology of integrated circuits so that a major part of the electronics required in the equipment is inherent in the structure of the detector means itself.
FIG. 11B is a view, on an enlarged scale, partly in section, of the solid state unit of the detector means of FIG. 11A.

As hereinbefore observed, the scintillation coatings 10a and 10b may be replaced with a detector which may even extend over the entire sector $\beta$ shown in FIG. 6. The detector may be implemented, for example, by using the production technique of integrated circuits. In such case, a plurality of those functions may be accommodated in the structure of the detector itself, which in FIG. 5 are assigned to the electronic units 22, 23, 24 and 25. In this, no fiber optic cables 21a and 21b are needed, either. Instead, an electrical signal is directly obtained from the coating and on the basis of such signal the stresses to be measured may be detected. This embodiment is schematically shown in FIGS. 11A and 11B, wherein a series $50 = 50_1...50_N$ of photodiodes (N in number) arranged substantially in the direction of the inclination axis A—A is used as the detector 10. A fluorescent film 46 is integrated into the series 50. When an X-ray hits the film 46, it emits a photon, and the photodiode $50_N$ in this location provides a voltage, which is supplied by a square wave generator 40, for example (not shown in the Figs.). The voltage pulse changes the state of a bistable multivibrator 43, or the equivalent, when an X-ray X excites a photon in the adjacent diode $50_N$. The multivibrator 43, or the equivalent, may be incorporated in the integrated structure of the detector 10, which is arcuate in shape in the manner hereinbefore described. The changes of state of the multivibrator 43 are recorded by a fast scanner 44, and the electrical signal produced in this manner is input to the computer 45. Instead of the bistable multivibrator 43 and scanner 44, a digital counter may be used directly and records the number of voltage pulses arising from the detector 10.

The absorption and sending of X-rays Xa and Xb takes place in the bulk silicon 46 below the surface of the photodiode array 50. The entire surface of the photosensor region is covered by a passivating layer of silicon dioxide 49 one $\mu$ m thick permitting exposure to the ambient atmosphere. The mechanism sensing the charge developed by current sources in the silicon is derived from the properties of the diode junctions of p+ strip diode elements $50_1...50_N$ and the n-type substrate 47. Periodically, the scanning circuit cycles through the array 50, connecting each p+ region in turn to bias lines, also called video lines, (not shown in the Figs.) that run along either side of the photodiode array 50. During the short time that contact is maintained for each diode element $50_1...50_N$, the voltage on the line reverse-biases the diode and forms a shallow depletion layer 48 at the junction. Even after contact with the bias line is broken by the scanning circuit, the depletion layer 48 is maintained by charge stored at its boundaries. The depletion layer 48 thus appears as a capacitor whose stored charge can be dissipated between scans only by current sources in the silicon. Principal sources are thermal dark current and photocurrent arising from photon absorption. The extent to which these sources discharge the depletion layer 48 is sensed at the same time that the diodes $50_1...50_N$ are sequentially biased in consecutive scan cycles. At room temperature, the period between consecutive scans, and hence the signal integration time of the photodiodes $50_1...50_N$ has an upper limit to several hundred milliseconds so that the dark current alone will not completely discharge the depletion layer 48.

It should be apparent to these skilled in the art that any X-ray diffraction detector for measuring stresses in austenitic steels or similar metals must be capable of operating in the specific ranges of X-rays diffracted from such metals, i.e., a range from the K$\alpha$ characteristic radiation of 5.4 keV for chromium to the K$\alpha$ characteristic radiation of 17.4 keV for molybdenum.

Moreover, these radiation energies diffracted by the austenitic steel or similar metal must be generated by an X-ray tube capable of producing at least 40 keV acceleration voltages which will impinge upon the specimen under stress analysis.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in the limiting sense.

It is also to be understood that the following claims are intended to cover all of the generic and specific features of the invention herein described, and all statements of the scope of the invention which, as a matter of language, might be said to fall therebetween.

What is claimed is:

1. X-ray diffraction apparatus for measuring the stress state at a point on a metallic specimen, comprising:

X-ray means for producing monochromatic X-rays comprising photons having a characteristic energy in the range of between about 5.4 to 17.5 keV;

selectively adjustable mounting means for directing incoming X-rays to impinge on the specimen at a point whose stress state is to be measured at a selected on of at least two inclination angles with respect to an axis passing through said point in a direction substantially perpendicular to the strain effect of the stress to be measured;

means for detecting and measuring the stress state at said point, said detecting and measuring means including integrated solid state position-sensitive photosensor means located on at least one side of said incoming X-rays, said integrated photosensor means being positioned and sized so that X-rays diffracted from the specimen impinge on it, said photosensor means comprising a plurality of components spaced from each other in the direction of the inclination axis for directly converting photons of said diffracted X-rays that impinge thereon into electrical signals, and said detecting and measuring means further including circuit means coupled to said photosensor means, said circuit means comprising counting means for detecting said electrical signals and measuring the number of photons impinging on each of said components of said solid state photosensor means.

2. The apparatus of claim 1 wherein said circuit means further comprises means coupled to said photon measuring means for determining the stresses being measured.

3. The apparatus of claim 1 wherein said integrated solid state photosensor means are located symetrically on both sides of said incoming X-rays.

4. The apparatus of claim 1, wherein said integrated solid state photosensor means comprise an integrated photodiode array having a fluorescent film on which said diffracted X-rays impinge.

5. The apparatus of claim 1, wherein said integrated solid state photosensor means comprises an integrated series of bistable multivibrators.

6. The apparatus of claim 1, wherein said circuit means comprises recording means connected to said integrated solid state photosensor means and a computer connected to said recording means.

7. The apparatus of claim 6, wherein said recording means comprises rapid scanner means.

8. The apparatus of claim 6, wherein said recording means comprises a digital counter.

9. The apparatus of claim 1, wherein said circuit means comprises an analog to digital converter for receiving said electrical signals from said photosensor means, said analog to digital converter producing a digital signal output and said circuit means further comprises a multi-channel analyzer connected to said analog to digital converter so as to receive said digital signal output and to produce an output signal of its own, a computer connected to said multi-channel analyzer so as to receive said output therefrom, a graphic display unit, and a digital input printer, said computer being programmed to convey the results of stress measurement of said metal object to said graphic display unit and to said digital input printer such that said results can be therein converted to printed form.

10. The apparatus of claim 9, further comprising a high voltage source for said X-ray means, and said computer being connected to and controlling said high voltage source for providing a suitable measuring sequence.

* * * * *

REEXAMINATION CERTIFICATE (3444th)
United States Patent [19]
Korhonen et al.

[11] B1 5,125,016
[45] Certificate Issued Feb. 24, 1998

[54] PROCEDURE AND MEASURING APPARATUS BASED ON X-RAY DIFFRACTION FOR MEASURING STRESSES

[75] Inventors: Matti Korhonen; Veikko Lindroos, both of Espoo, Finland

[73] Assignee: Outokumpu Oy, Espoo, Finland

Reexamination Request:
No. 90/004,488, Jan. 13, 1997

Reexamination Certificate for:
Patent No.: 5,125,016
Issued: Jun. 23, 1992
Appl. No.: 530,896
Filed: May 30, 1990

Related U.S. Application Data

[63] Continuation-in-part of Ser. No. 740,073, May 20, 1985, abandoned.

[30] Foreign Application Priority Data

Sep. 22, 1983 [FI] Finland .................. 833393

[51] Int. Cl.[6] .................. G01H 23/20
[52] U.S. Cl. .................. 378/72; 378/70; 378/79; 378/197; 250/370.1
[58] Field of Search .................. 378/72, 71, 70, 378/73, 81, 79

[56] References Cited

U.S. PATENT DOCUMENTS

| | | | |
|---|---|---|---|
| 3,639,758 | 2/1972 | Shimura | 250/51.5 |
| 3,663,812 | 5/1972 | Koenig et al. | 250/49.5 PE |
| 3,784,816 | 1/1974 | Abrahamsson | 250/273 |
| 3,859,525 | 1/1975 | Ashe et al. | 250/273 |
| 3,868,506 | 2/1975 | Ogiso | 250/278 |
| 3,934,138 | 1/1976 | Bens | 250/278 |
| 3,982,127 | 9/1976 | Hartmann et al. | 250/273 |
| 4,095,103 | 6/1978 | Cohen et al. | 250/277 |
| 4,131,794 | 12/1978 | Bruninx | 250/272 |
| 4,489,425 | 12/1984 | Borgonovi | 378/72 |

FOREIGN PATENT DOCUMENTS

| | | |
|---|---|---|
| 0117293 | 9/1984 | European Pat. Off. . |
| 3236109 | 4/1983 | Germany . |
| 46-109935 | 8/1973 | Japan . |
| 4819797 | 10/1974 | Japan . |
| 52-89763 | 7/1977 | Japan . |
| 2083215 | 3/1982 | United Kingdom . |

OTHER PUBLICATIONS

"X-Ray Technique Manual", edited by V.V. Klyver, Book 2, 1980, pp. 308-311.

(List continued on next page.)

*Primary Examiner*—David P. Porta

[57] ABSTRACT

Procedure based on X-ray diffraction for measuring the stress state of metals, in particular austenitic steels. In the procedure the detector surface (10) is inclined about the axis (A—A) lying on the surface of the sample (20) being examined which is substantially perpendicular to the direction of the stresses ($\sigma_{xx}$) being examined. By means of the detector surface (10) the diameters ($2S_{ax}$) of the so-called Debye rings in the direction of the surface being examined are recorded at two or several inclination angles ($\psi$). The detector surface (10) has arcuate shape, as viewed in the direction (B—B) at right angles against the inclination axis (A—A), and in the procedure is used such as arcuate detector surface (10) elongated in the direction of said inclination axis (A—A) and narrow enough in the opposite direction that an inclination angle ($\psi$) of the detector surface (10) large enough in view of the procedure's implementation is feasible. In the procedure a detector surface (10) is used by which the x-rays reflected from the sample are converted to photosignals, and that on the basis of these photosignals the stresses to be measured are determined. Also disclosed is a measuring instrument in which the detector surface (10) is located symmetrically on both sides of the collimator, and the detector surface (10) is provided with elements (10a, 10b;41) by which the X-ray radiation incident on the detector surface is converted into photosignals, and the apparatus further comprises a unit or units with which the stresses to be measured are derived on the basis of the photosignal.

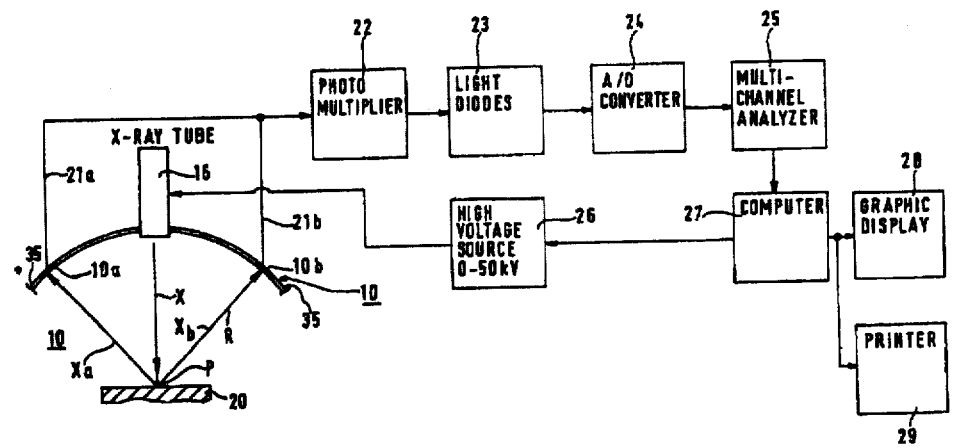

OTHER PUBLICATIONS

P. Doig and P.E.J. Flewitt, "Non–destructive stress measurement using X–ray diffraction methods", NDT International, Jun. 1978, pp. 127–131.

Clayton O. Ruud, "X–Ray Analysis and Advances in Portable Field Instrumentation", Journal of Metals, Jun. 1979, pp. 10–15.

Korhonen, M.A., et al., "Determination of Shear Stresses by a new Solid State X–Ray Camera System", Helsinki University of Technology, (1989), pp. 265–270.

C.O. Ruud, "A review of selected non–destructive methods of residual stress measurement", NDT International, Feb. 1982, pp. 15–23.

Ismail C. Noyan, et al., "Residual Stress", Springer–Verlag, (1987), Table of Contents and pp. 103–108.

D.A. Steffen, et al., "A Versatile Position Sensitive X–Ray Detector", U.S. Army MERDCOM, pp. 309–315.

Clayton O. Ruud, "Position–sensitive detector improves x–ray powder diffraction", Industrial Research and Develoopment, Jan. 1983, pp. 84–87.

Herbert E. Göbel, "A New Method for Fast XRPD Using a Position Sensitive Detector", Plenum Press, New York vol. 22, (1979), pp. 255–265.

James Janesick, et al., "CCD advances for X–ray scientific measurements in 1985", SPIE vol. 597 X–Ray Instrumentation in Astronomy, (1985), pp. 364–380.

Matti Korhonen, "On the Improvement of the Accuracy of X–Ray Stress Measurement by Camera Methods", Helsinki University of Technology, (1980), pp. 1–93 and Appendixes A–D.

Harry Zantopulos, et al., "Systematic Errors in X–Ray Diffractometer Stress Measurements Due to Specimen Geometry and Beam Divergence", Adv. in X–ray Anal., vol. 14, 360 (1971), pp. 360–376.

M.A. Short, et al., "Intensity Correction Factors for X–Ray Diffraction Measurements of Residual Stress", Adv. in X–ray Anal., vol. 16, 379 (1973), pp. 379–389.

Carol J. Kelly, et al., "Errors in Residual Stress Measurements Due to Random Counting Statistics", Adv. in X–Ray Anal., vol. 14, (1971), pp. 378–387.

Fairchild: CCD, The Solid State Imaging Technology, "Technical Note on X–Ray Imaging with Fairchild CCD Image Sensors", by R.H. Dyck, Jun. 1981.

Reticon: Image Sensing Products, pp. 165–168.

K. Simomaa, et al., "X–Ray Detection using a CCD Device and its Application to Synchrotron Radiation Imaging and Stress Management", Conf. on Image Detection and Quality, Jul. 16–18, 1986, Paris, France, pp. 203–207.

E.G. Chowanietz, et al., "Charge coupled devices (CCDs) for X–ray spectroscopy applications", SPIE vol. 597, X–Ray Instrumentation in Astronomy (1985), pp. 381–388.

B. D. Cullity, "Elements of X–ray Diffractions", Addison––Wesley Reading, Mass., 1956, pp. 13–15 and 509–513.

M.A. Korhonen, et al., "Application of a new Solid State X–Ray Camera to Stress Measurement", Adv. in X–Ray Anal., vol. 32, (1989), pp. 407–413.

L.S. Gorn, et al., "Position–Sensitive Detectors", Energoizdat Publishers, (1982), (pp. 1–8 of English translation).

E.A. Kooper, et al., "Measuring Parameters of a Linear CCD Structure as a Detector of One–Dimensional X–Ray Images", USSR Academy of Sciences, et al., (1982), All–Union Conference on Utilization of Synchrotron Radiation SI–82, pp. 4–12 of English translation.

Denver Research Institute, "Design and Fabrication of an X–ray Stress Analyzer", Jun., 1981.

Koppel, L. "Direct X–ray Response of Self–Scanning Photodiode Arrays", *24th annual Conf. Appl. of X–ray Analysis*, Aug. 1975, pp. 587–596.

McGinnis, John, "X–ray Sensitive Photodiode Array," *Industrial Research & Development*, Mar. 1980, pp. 143–146.

McGinnis, et al. "X–ray Applications of Self–scanned Photodiode Arrays" *Inter. Adv. in Nondestructive Testing*, 1981, vol. 8, 201–16.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-10 is confirmed.

* * * * *